United States Patent [19]

Strock

[11] 4,211,330

[45] Jul. 8, 1980

[54] ORAL HEALTH AND HYGIENE KIT

[76] Inventor: Alvin E. Strock, 647 Commonwealth Ave., Newton Center, Mass. 02159

[21] Appl. No.: 8,612

[22] Filed: Feb. 1, 1979

[51] Int. Cl.² .................. A45B 15/00; A61C 15/00
[52] U.S. Cl. .................... 206/581; 206/229;
   206/38; 206/37; 206/63.5; 206/823; 15/110;
   128/62 A; 132/79 A; 132/84 A; 132/90
[58] Field of Search .............. 15/106, 110, 167 R,
   15/210 R, 227; 32/40 R; 128/62 A; 132/79 R,
   79 A, 79 E, 84 R, 84 A, 84 B, 84 D, 85, 89-90;
   206/37-38, 63.5, 229, 361, 368, 581, 823;
   401/130

[56] References Cited

U.S. PATENT DOCUMENTS

| | | | |
|---|---|---|---|
| 1,439,076 | 12/1922 | Edwards | 206/63.5 X |
| 1,519,515 | 12/1924 | Stonehill | 132/84 A |
| 1,626,310 | 4/1927 | Tipton | 132/84 A |
| 2,512,001 | 6/1950 | Terry | 132/79 E |
| 2,601,244 | 6/1952 | Boulicault | 132/84 B |
| 2,621,784 | 12/1952 | Van Boytham | 206/361 |
| 3,368,668 | 2/1968 | Micciche | 206/229 |
| 3,534,887 | 10/1970 | Ginsberg | 132/79 A X |
| 3,902,509 | 9/1975 | Tundermann et al. | 206/229 X |
| 3,952,867 | 4/1976 | McCord | 132/84 R X |
| 4,105,120 | 8/1978 | Bradberry | 206/581 |

*Primary Examiner*—Herbert F. Ross
*Attorney, Agent, or Firm*—Cesari & McKenna

[57] ABSTRACT

An oral health and hygiene kit comprises a length of flexible liquid pervious material, said length of material including a pocket for containing a finger. A dentifrice is applied to an exterior face of the pocket. Also the length of material extends longitudinally away from the opening into the pocket and a transverse sleeve is formed in the extension for containing a length of dental floss and a relatively rigid dental stimulator.

6 Claims, 3 Drawing Figures

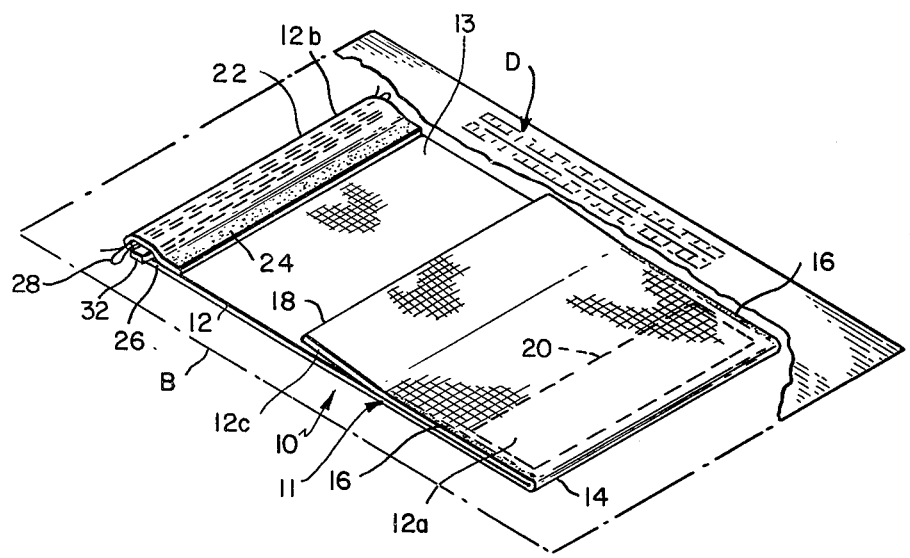
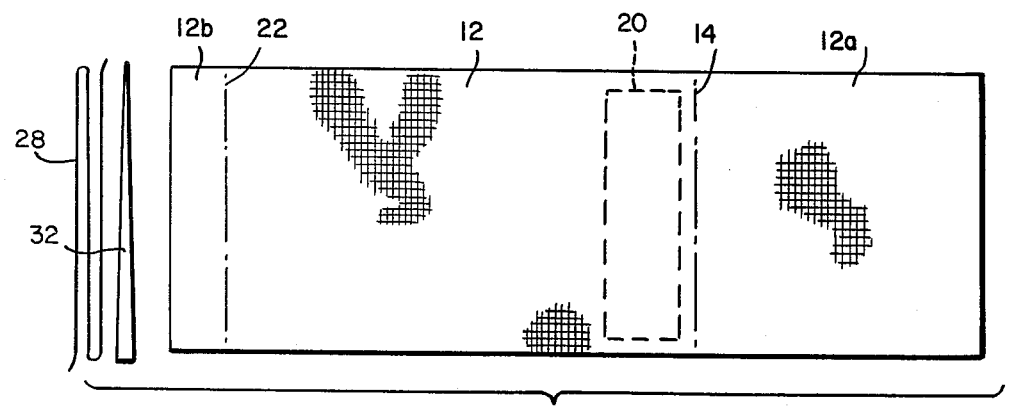
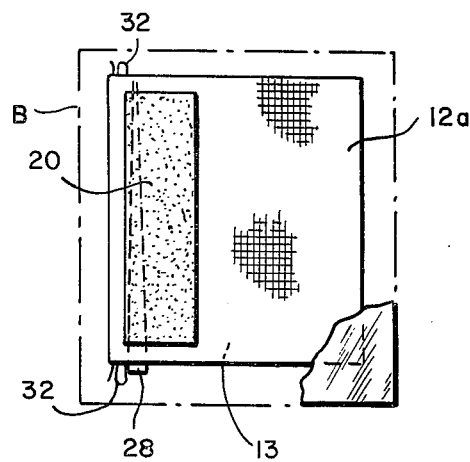

ORAL HEALTH AND HYGIENE KIT

This invention relates to an oral health and hygiene kit. It relates more particularly to a readily portable, disposable, finger operable periodontal massaging device which enables a user to massage his gums and remove plaque from his teeth and gums at any desired time and place during the day. The massaging device may carry a dentifrice or other material which facilitates plaque removal. The massaging device may also function as a holder for dental floss and a dental stimlator and therefore serve as a complete dental health and hygiene package.

BACKGROUND OF THE INVENTION

Finger-operable cots and pads for applying dentifrice to teeth and for massaging the gums have been known for many years. Examples of such devices are disclosed in U.S. Pat. Nos. 1,343,713, 2,176,308 and 3,608,566. Generally these devices include a pad an area of which is coated or impregnated with dentifrice. The user rubs the coated or impregnated area of the pad over the teeth and gums to massage and clean them. The package described in the last-mentioned patent includes an envelope tearstring which can be used to clean between the teeth.

These prior devices have various disadvantages which have limited their use and effectiveness as promotors of oral health and hygiene. Most prior devices are designed primarily to remove food particles from the teeth and to refresh the breath, with little or no attention being paid in their design to the importance of proper periodontal massage and plaque removal to oral health. While brushing is recognized as an important and effective mechanism for plaque removal, few people take the time to brush after each meal during the day and most people limit their brushing activities to the early morning and perhaps also to the late evening before retiring. There thus are long periods of each day during which food particles are allowed to remain on and between the teeth and gums and during which harmful plaque is allowed to build up. Also, most dental practitioners recognize that brushing has, at best, only a minimal benefit in periodontal stimulation. In fact, an increasing number of such practioners are finding that brushing can have a harmful effect in terms of tooth abrasion and gum irritation. Such practioners generally recommend periodontal massage as a supplement to brushing. Such massage increases blood circulation in, and exercises, the soft gum tissue, giving rise to stronger, healthier gums.

Some prior devices of the type mentioned above are also difficult to use. For example, the pad-type applicator disclosed in the aforementioned U.S. Pat. No. 2,176,308 is difficult to grip with the fingers and to manipulate in the mouth because the dentifrice which is supposed to adhere the pad to the finger becomes diluted and dissolves upon contact with the saliva present in the mouth causing the pad to slip relative to the manipulating finger. Therefore, the user is usually required to grasp the pad between fingers in order to properly move it around within the mouth.

Further, in some cases the prior devices are quite large relative to the finger so that when manipulated within the mouth, the pads fold and become wrinkled making them difficult to control and so that dentifrice is not always in contact with the teeth as the pad is moved around within the mouth. As for those devices like the one disclosed in the aforementioned U.S. Pat. No. 3,608,566 which are supplied in an envelope having a tearstring which may function as dental floss, the tearstring is associated with the envelope rather than the dentifrice applicator. Consequently, the floss is frequently lost or thrown away with the envelope.

Finally, none of the prior devices of this general type of which I am aware include as an integral part thereof a dental stimulator which can be used in conjunction with the dentifrice applicator and dental floss provided therewith to facilitate removing particles and plaque from between the teeth.

SUMMARY OF THE INVENTION

Accordingly, this invention aims to provide an improved oral health and hygiene kit.

Another object of this invention is to provide a readily portable disposable, finger operable device which is designed specifically to facilitate periodontal massage and plaque removal and which serves as an ideal supplement to brushing, particularly during times when brushing is not practical.

Another object is to provide a device of the type described that may carry a quantity of dentifrice or other material that facilitates plaque removal.

Another object is to provide a device of the type described that protects the dentifrice it carries and prevents it from being damaged or stripped away and cracked as the device proceeds through commercial channels to the ultimate user.

A further object of the invention is to provide a device of the type described that carries dental floss and a dental stimulant to provide for even more effective food particle and plaque removal.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, an oral health and hygiene kit according to this invention comprises a water-pervious, relatively soft, flexible, textured periodontal massaging pad having a pocket for relatively loosely engaging over a person's finger, preferably the index finger. A quantity of dentifrice or other plaque removal material may be adhered to one exterior face of the pocket near the bottom thereof. The pad also includes a flap integral with a top edge of the pocket, the flap being substantially the same width as the pocket. The flap enables the pad to be maintained on the finger by gripping with the thumb. A sleeve may be formed at the end of the flap remote from the pocket. Contained within the sleeve may be a length of dental floss and a dental stimulator.

The massaging pad with the floss and stimulator mounted therein as aforesaid constitute a disposable oral health and hygiene kit which can be packaged individually or in any suitable number in a plastic envelope or other appropriate container, suitable instructions for use of the kit being provided on the outside of the envelope or container.

In order to condition his mouth, the user places his index finger in the massaging pad pocket, grips the pad flap with his thumb and inserts the pad into his mouth with the dentifrice area facing the teeth and gum areas. The rigid dental stimulator in the pad sleeve facilitates the gripping of the flap with the thumb. The user then proceeds to gently press and rub his gums, thereby to stimulate circulation and exercise his gums. The textured, relatively rough surface of the pad provides a maximum amount of stimulation to the gums. The saliva present in the user's mouth gradually dissolves the binder components of the dentifrice as the user rubs the massaging pad over his gums and teeth thereby to gradually release the abrasive particles which facilitate the removal of food particles and plaque from the teeth and gums. The dental floss and dental stimulant may be removed from the sleeve when desired to facilitate cleaning between the teeth.

To minimize damage to the kit during handling, it can be packaged in its envelope with its flap folded over the pocket so that the rigid dental stimulator overlies the dentifrice area. Consequently the stimulator functions as a reinforcing beam or strut to minimize the likelihood of the dentifrice being bent or cracked during handling of the kit, particularly if it is packaged in a relatively flimsy flexible envelope.

Yet with all of its aforesaid advantages, the present kit should still be relatively inexpensive to manufacture and market. Therefore it should find wide application as a healthful supplement to brushing for enhanced plaque removal and periodontal stimulation particularly during those times of day when brushing is not practical. The kit may also prove useful in situations where potential users are traveling or otherwise away from home and where their regular toothbrush, waterjet or other conventional oral cleaning appliances are not readily available.

BRIEF DESCRIPTION OF THE DRAWING

For a fuller understanding of the nature and objects of the invention, reference should be had to the following detailed description taken in connection with the accompanying drawing, in which:

FIG. 1 is a perspective view of a packaged oral health and hygiene kit made in accordance with this invention;

FIG. 2 is a top plan view on a slightly smaller scale showing the massaging pad component of the kit partially assembled and showing the other kit components in greater detail, and FIG. 3 is a similar view on a still smaller scale showing a packaged folded version of the kit.

DESCRIPTION OF THE PREFERRED EMBODIMENT

Referring now to FIG. 1 of the drawing, my kit indicated generally at 10 is packaged in a transparent plastic or cellophane envelope or bag B, suitable directions D for using the kit being imprinted on the outside of the bag. Kit 10 comprises a relatively long generally rectangular massaging pad 11 made of a strip 12 of a liquid pervious absorbent, relatively soft, flexible, textured material. The desired surface texture may be provided using an open weave material. A suitable material is the woven rayon fabric which is the same open weave fabric used to make disposable washcloths of the type sold under the trademark Handi-Wipe.

Turning to FIGS. 1 and 2, one end portion 12a of the strip 12 is folded along a transverse fold line 14 so that it lies flush against the strip with the side edges of portion 12a being adhered to the underlying side edges of the strip by waterproof glue lines 16 or other comparable means such as weaving lines, so as to define a relatively wide rectangular pocket 18. The remainder of strip 12 constitutes an integral flap 13 which extends above the pocket. Adhered to one exterior face of pocket 18 near fold line 14 is quantity of a suitable dentifrice 20 or other material that facilitates plaque removal. The dentifrice 20 is extruded, printed, deposited or otherwise applied to strip 12 in a flowable state so that at least some of the dentifrice penetrates into the openings in the open weave material of strip 12. Then when the dentifrice material hardens due to contact with air, mechanical bonds are formed between the dentifrice and strip 12 material so that the dentifrice 20 is securely anchored to the fabric strip.

The opposite end portion 12b of strip 12 at the end of flap 13 is also folded back on itself along a transverse fold line 22. The end edge of strip 12 is adhered to the face of the strip along a transverse waterproof glue or weaving line 24 forming a relatively narrow transverse sleeve 26 which extends the width of the strip. Positioned within sleeve 26 is a length of dental strip material 28 and a dental stimulator in the form of a thin, relatively stiff, tapered pick 32 made of wood, plastic or other similar material. These components are shown completely in FIG. 2. The dental strip material 28 may be conventional dental floss, as illustrated in the drawing, or dental tape, which floss or tape may or may not be coated with a suitable plaque removal material. Preferably at least one end of the length of floss 28 projects out of the sleeve as shown so that the floss can be withdrawn easily from the sleeve. Preferably also the pick 32 extends the full length of the sleeve for reasons that will become apparent later. The pick 32 may be of the type sold by Johnson & Johnson under the trademark Stimudent.

Thus the complete kit 10 includes the massaging pad 11 which supports the dentifrice 20 at one end and encloses the floss 28 and dental stimulator 32 at its other end. Those components are contained within a protective envelope B until it is time to use them.

In use, the kit 10 is first removed from envelope B. Then the user inserts a finger, preferably the index finger, into pocket 18 so that the front of the finger engages behind the dentifrice 20. The pocket is sufficiently deep that it tends to remain on the finger particularly since the strip 12 material is relatively coarse so that there is an appreciable amount of friction between the surface of the finger and the inside of the pocket. The flap 13 is pressed by the thumb of the same hand against the palm of the hand to hold the pad in place over the finger. With the rigid dental stimulator 32 in the sleeve 26 the grip on the flap 13 is facilitated. Also if desired, the length of the glue or weaving line 16 at one or both sides of pocket 18 can be made to stop short of the top of the pocket to provide a loose flap so that the two faces of the pocket are separated as shown at 12c in FIG. 1. This permits the finger to be oriented at an angle within the pocket which for some people may facilitate moving the massaging pad within the mouth. By providing such a shortened glue or weaving line 16 on only one side of the pocket 18, the pad can be made preferentially either a right handed or left handed device.

The pad 11 is then inserted into the mouth with the dentifrice 20 facing the teeth. The pad 11 is then used to gently press and rub the gums and to provide the proper periodontal massage. Saliva present in the mouth gradually dissolves the binder components of the dentifrice and gradually frees the abrasive components thereof to provide additional abrasive action to clean the teeth and remove plaque therefrom and from the gums. The fact that the strip 12 is made of a relatively coarse textured material enhances the massaging and plaque removal action. The dental floss 28 and stimulator 32 can be removed from the sleeve 26 when desired by the user to clean between the teeth. Of course, once used, the kit 10 components can be thrown away.

FIG. 3 illustrates a slightly modified kit version which has certain advantages over the FIGS. 1 and 2 embodiment and which make it particularly suitable when each kit is packaged individually. As seen from FIG. 3, the pad flap 13 is folded back onto pocket 18 so that the sleeve 26 overlies the dentifrice 20. This produces two distinct advantages. First, the overall kit has less areal extent and therefore it can be packaged in a smaller envelope. Secondly, the relatively rigid pick 32 overlying the entire length of the dentifrice 20 functions as a reinforcing beam or rib which inhibits transverse folding or bending of the stripe 20 which distortions might tend to cause the stripe to crack or break or pull away from the strip 12 material. Thus the kit depicted in FIG. 3 can be handled relatively roughly without the dentifrice stripe 20 becoming damaged or dislodged from the pad.

The components of the subject kit can be manufactured on a continuous high volume basis using conventional cutting, folding, glueing and inserting apparatus that operate in other contexts on web drawn continuously from a roll. If desired, a removal cover (not shown), such as of thin metal foil or the like, can be lightly adhered over the dentifrice 20 as a further protection and to prevent excessive drying of the dentifrice 20 with time. Therefore, despite the aforesaid advantages, the present oral health and hygiene kit should not cost any more than prior comparable disposable finger cots and applicator pads.

It will thus be seen from the foregoing that the objects set forth above, among those made apparent from the preceding description are efficiently attained, and since certain changes may be made in the above constructions without departing from the scope of the invention as defined by the appended claims, it is intended that all matter contained in the above description or shown in the accompanying drawing be interpreted as illustrative and not in a limiting sense.

It should be understood that the word "dentifrice" as used in the appended claims is intended to cover not only conventional abrasive tooth pastes, powders and liquids, but also any other material that facilitates the removal of plaque from the teeth and soft tissue of the mouth.

It is also to be understood that the following claims are intended to cover all of the generic and specific features of the invention herein described.

I claim:

1. An oral health and hygiene kit including a periodontal massaging pad comprising a length of liquid pervious, flexible, textured material, means defining a pocket in said material length for engaging over a finger of a user, means defining an integral flap extending exteriorly of said pocket for gripping by a thumb to retain the pad on the finger during inserting and manipulation of said pad within the mouth of a user, said periodontal pad further including means defining an open ended receptacle in said integral flap and wherein said kit further includes means for removing food particles retained within said receptacle, said means for removing food particles comprises a length of dental floss and a rigid dental stimulator.

2. The kit defined in claim 1 further including a quantity of dentifrice adhered to a portion of said massaging pad defining said pocket.

3. The kit defined in claim 2 wherein said receptacle is a transverse sleeve formed in said material length exteriorly of said pocket and said dental stimulator comprises a rigid pick contained in said sleeve.

4. The kit defined in claim 2 wherein said dentifrice is organized to extend transversely across the face of said pocket and said sleeve extends transversely across the length of material with said dental stimulator extending the full length of the sleeve so that when the length of material is folded so that said sleeve overlies said pocket, said dental stimulator is superimposed on the dentifrice so as to function as a reinforcing beam to help prevent said dentifrice from being bent or folded as the kit is being handled.

5. The kit defined in claim 2 wherein said liquid pervious flexible, textured material is an open weave fabric material.

6. Component parts arranged in an oral health and hygiene kit, said parts comprising a length of textured flexible material, means defining a transverse pocket in said length of material, a quantity of dentifrice extending transversely across the exterior face of the pocket, said length of material having a flap extending longitudinally relative to the opening into said pocket, means defining a transverse sleeve across a portion of the flap spaced from the opening into the pocket, a length of flexible dental strip material positioned within the sleeve and a relatively rigid dental stimulator positioned in the sleeve and extending substantially the full length thereof.

* * * * *